(12) United States Patent
Rey et al.

(10) Patent No.: US 10,080,907 B1
(45) Date of Patent: Sep. 25, 2018

(54) SYSTEMS AND METHODS FOR CONTROLLING THE SPATIAL DISTRIBUTION OF AN ELECTROMAGNETIC FIELD

(71) Applicant: Valerie Llewellyn, Madeira Beach, FL (US)

(72) Inventors: Jose I. Rey, Tampa, FL (US); Richard Gilbert, Tampa, FL (US); John Anthony Llewellyn, Tampa, FL (US); Richard J. Connolly, Riverview, FL (US); Mark Jaroszeski, Tampa, FL (US); Andrew M. Hoff, Tampa, FL (US)

(73) Assignee: University of South Florida, Tampa, FL (US)

( * ) Notice: Subject to any disclaimer, the term of this patent is extended or adjusted under 35 U.S.C. 154(b) by 1255 days.

(21) Appl. No.: 14/065,340

(22) Filed: Oct. 28, 2013

Related U.S. Application Data

(60) Provisional application No. 61/719,091, filed on Oct. 26, 2012.

(51) Int. Cl.
*A61N 5/00* (2006.01)

(52) U.S. Cl.
CPC ...................................... *A61N 5/00* (2013.01)

(58) Field of Classification Search
None
See application file for complete search history.

(56) References Cited

U.S. PATENT DOCUMENTS

| | | |
|---|---|---|
| 1,908,688 A | 5/1933 | Call |
| 3,918,461 A | 11/1975 | Cooper et al. |
| 4,074,718 A | 2/1978 | Morrison, Jr. et al. |
| 4,535,777 A | 8/1985 | Castel |
| 4,637,397 A | 1/1987 | Jones et al. |
| 4,800,883 A | 1/1989 | Winstrom |
| 5,468,223 A | 11/1995 | Mir |
| 6,850,802 B2 | 2/2005 | Holsheimer |
| 6,858,000 B1 | 2/2005 | Igorevich |
| 7,160,241 B1 | 1/2007 | Herbst |
| 7,668,592 B2 | 2/2010 | Heller et al. |
| 8,048,067 B2 | 11/2011 | Davalos et al. |
| 8,152,801 B2 | 4/2012 | Goldberg et al. |

(Continued)

FOREIGN PATENT DOCUMENTS

WO     2007044386     4/2007

OTHER PUBLICATIONS

Jose Rey, "Guiding Electric Fields for Electroporation Applications", USF, Scholar Commons, Graduate School Theses and Dissertations, Jan. 1, 2011.

(Continued)

*Primary Examiner* — Kaitlyn Smith
(74) *Attorney, Agent, or Firm* — Thomas | Horstemeyer, LLP

(57) ABSTRACT

In one embodiment, controlling the spatial distribution of an electromagnetic field in a system involves determining an inflection frequency for energy applied to the system below which a first spatial distribution results and above which a second spatial distribution results, selecting an excitation frequency to be used to generate an electromagnetic field to be applied to the system based upon the determined inflection frequency, and applying an electromagnetic field generated using the selected excitation frequency.

25 Claims, 16 Drawing Sheets

(56) References Cited

U.S. PATENT DOCUMENTS

| | | |
|---|---|---|
| 8,244,345 B2 | 8/2012 | Palti |
| 2009/0012515 A1 | 1/2009 | Hoenig |
| 2009/0306654 A1 | 12/2009 | Garbagnati |

OTHER PUBLICATIONS

Dimova, et al., "Giant vesicles in electric fields, giant vesicles experiments over range of conductivities and frequencies", Soft Matter, 2007, 3, 817-827.

Rey, et al., "Electrostrictive Forces on Vesicles with Compartmentalized Permittivity and Conductivity Conditions", 2009 IEEE, 1280-1287.

SYSTEMS AND METHODS FOR CONTROLLING THE SPATIAL DISTRIBUTION OF AN ELECTROMAGNETIC FIELD

CROSS-REFERENCE TO RELATED APPLICATION(S)

This application claims priority to U.S. Provisional Application Ser. No. 61/719,091, filed Oct. 26, 2012, which is hereby incorporated by reference herein in its entirety.

BACKGROUND

Applied electromagnetic fields can be used in many diagnostic and therapeutic purposes. In such cases, electromagnetic fields are applied to biological tissue. Depending on the magnitude and duration of the power used, the fields can have different effects on the tissues. For example, low magnitude and extended duration of an electric potential can be used to drive charged therapeutic molecules through tissues in iontophoretic methods. High power electromagnetic fields in the radio and microwave frequencies can be used for tissue ablation to treat neoplastic diseases such as cancer. Energy packed in pulses with predominantly low frequency components can be used in combination with therapeutic molecules in electroporation and electropermeabilization. Pulses with components of higher magnitude and frequency, used in combination with therapeutic molecules or not, can be used in irreversible electroporation. Electromagnetic fields can also be used to excite tissues. In cardiac applications, electrodes can be used to apply enough power to excite heart tissues so that they are extrinsically activated, as in the case of cardiac pacemakers and defibrillators. Tissue excitation fields using lower power can also be used to excite tissues in the central and peripheral nervous tissue.

Although electromagnetic fields have been used in the above-noted therapeutic applications to positive effect, there is room for improvement. In many cases, the highest intensity of an applied field will be located in the tissue immediately proximate to the electrodes that are used to apply the field, which may not be the intended target for the energy. It would desirable if the spatial locations at which an electromagnetic field acts on a medium could be better controlled.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would desirable if the spatial locations at which an electromagnetic field acts on a medium could be better controlled. Disclosed herein are systems and methods for controlling the spatial distribution of an electromagnetic field within media, such as biological tissue. In some embodiments, an inflection frequency at which the spatial distribution of the electromagnetic field within the media changes is determined and, based upon that determination, an excitation frequency is selected to obtain a desired spatial distribution of field intensity.

In the following disclosure, various specific embodiments are described. It is to be understood that those embodiments are example implementations of the disclosed inventions and that alternative embodiments are possible. All such embodiments are intended to fall within the scope of this disclosure.

There is a fundamental relationship between media, such as biological tissue, and the excitation frequency used to apply an electromagnetic (e.g., electric) field to the media. By varying the excitation frequency, the spatial distribution and intensity of the electromagnetic fields can be controlled. Through such control, the electromagnetic fields can be focused on particular targets within the media.

Described below are systems and methods that exploit this fundamental relationship. The spatial distribution of an electromagnetic field varies as an excitation frequency is selected that is above or below the determined inflection frequency. The inflection frequency for a system depends upon the electrical properties of the system. In some cases, a volume of media may have several of these inflection frequencies. By electromagnetically exciting the media below and/or above the inflection frequencies, it is possible to deliver electromagnetic fields with different spatial distributions. Furthermore, the addition of two or more of these electromagnetic field distributions can produce a cumulative spatial field distribution to achieve a desired result within the media.

Figure 1:
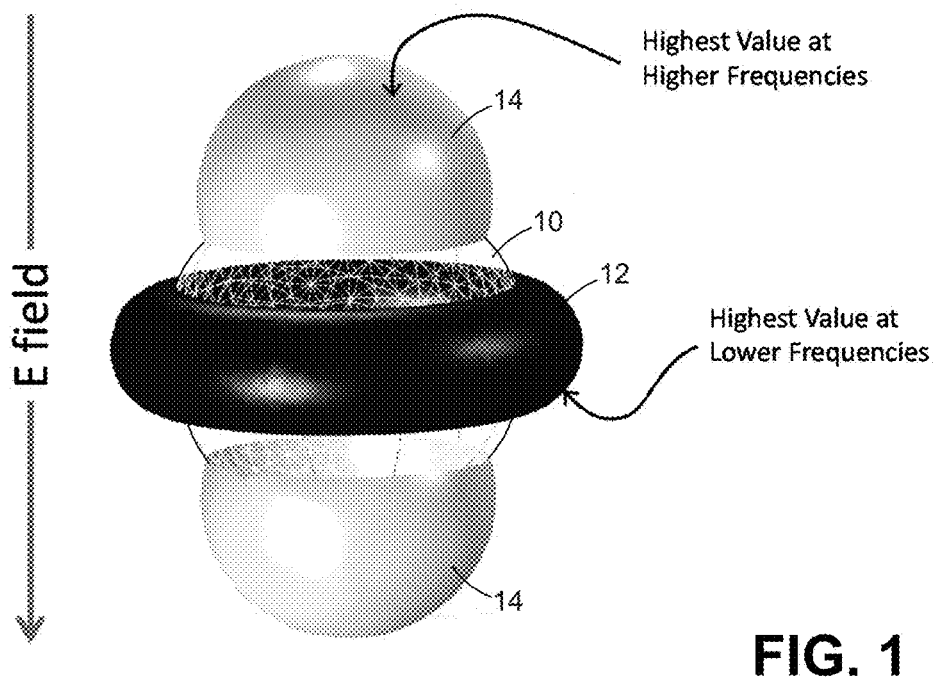
FIG. 1 is a diagram of an example system illustrating volumes containing highest electric field intensities applied to the system using different excitation frequencies.

FIG. 1 illustrates how different excitation frequencies affect the spatial distribution of an electromagnetic field. In this example, a sphere 10 within a cube represents a volume of media, such as biological tissue, to which an electric field, represented by the arrow E, is applied. When the electric fields result from applying a voltage or current that has a frequency below the inflection frequency of the system, the highest intensity of the field is focused within the volume identified by the torus 12, which encircles the sphere 10 around its center. If the applied voltage or current has a frequency that is above the inflection frequency, however, the highest intensity of the electric field is focused within two hemispherical volumes 14 located at the top and bottom of the sphere 10.

Figure 2:
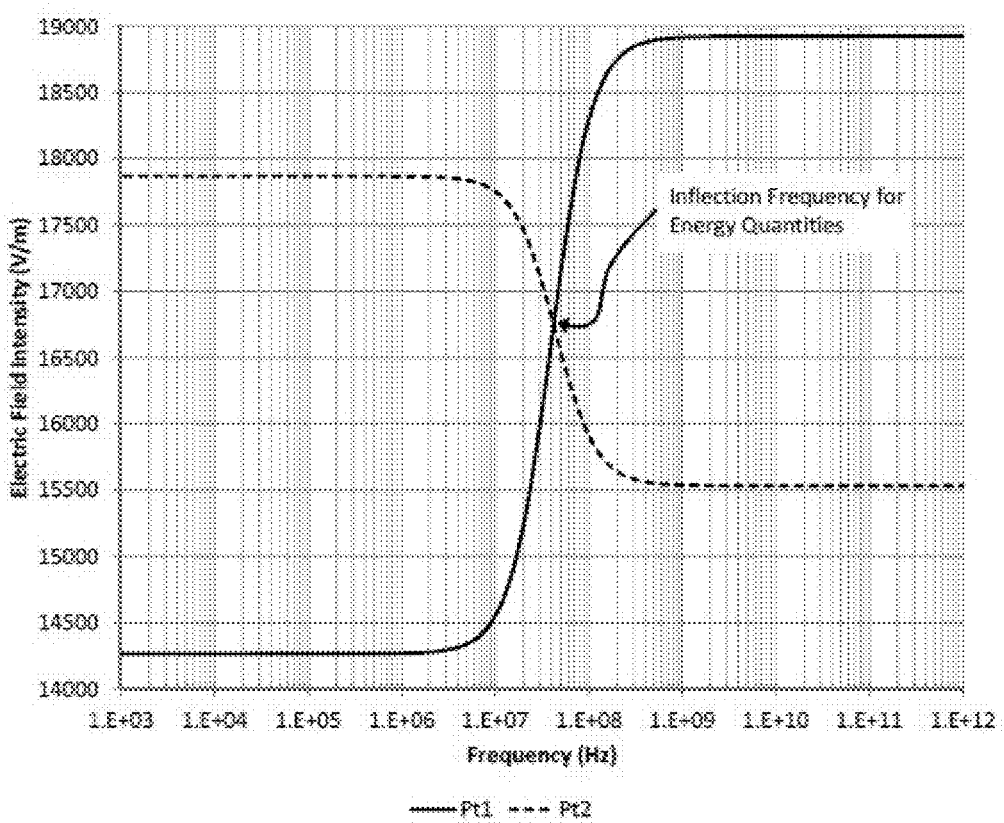
FIG. 2 is a graph that plots electric field intensity versus frequency at two different points in the system of FIG. 1.

The magnitudes of these two electric field distributions, as well as the inflection frequency, are shown in FIG. 2. In this figure, the solid line identifies the intensity of the electric field at a point on the top (14) of the sphere 10 and the dashed line identifies the intensity of the field at a point on the side of the sphere. As can be appreciated from FIG. 2, the intensity is greatest at the top of the sphere 10 when the excitation frequency (x axis of graph) is greater than the inflection frequency, which is approximately $3.5 \times 10^7$ Hz in this case. On the other hand, the intensity is greatest at the side (12) of the sphere 10 when the excitation frequency is lower than the inflection frequency.

In view of the above discussion, it can be appreciated that one can control the spatial distribution of an electromagnetic field within a system simply by knowing the inflection frequency of the system and selecting an excitation frequency based upon inflection frequency. In order to exercise such control, one must first know the inflection frequency for energy applied to the system. In some embodiments, this frequency can be determined by first determining a critical frequency of the system based upon electrical properties of the system and then correlating that frequency to the inflection frequency for energy applied to the system.

Figure 3:
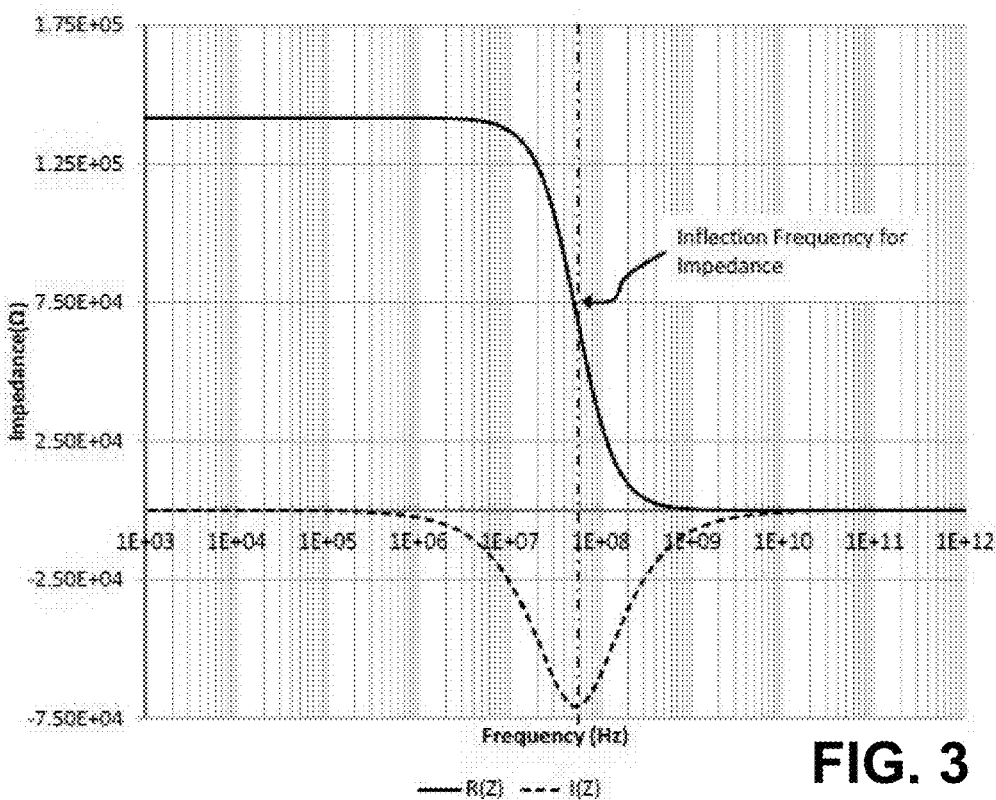
FIG. 3 is a graph that plots impedance versus frequency for the system of FIG. 1.

In some embodiments, the critical frequency of the system can be determined by measuring the impedance of the system as electromagnetic fields are applied to the system using various excitation frequencies and identifying an inflection point of those frequencies. In such a case, the critical frequency of the system can be referred to as the inflection frequency for the impedance of the system. FIG. 3 illustrates the results of such an exercise performed in relation to the system of FIG. 1. In particular, FIG. 3 illustrates the real (solid line) and imaginary (dashed line) components of the impedance of that system (which can have be determined either through modeling or measuring) as an electric field is applied to the system while sweeping the excitation frequency from a low value (1,000 Hz) to a high value ($1 \times 10^{12}$ Hz). The inflection frequency for the impedance of the system is the excitation frequency (x axis) at which an inflection point (i.e., change of slope) occurs within the real component of the impedance, the excitation frequency at which a local minimum occurs for the imaginary component of the impedance, or both. In the example of FIG. 3, the inflection frequency for the impedance of the system occurs at $5.5 \times 10^7$ Hz. As can be appreciated from FIG. 3, the real component of the impedance changes slope and the imaginary component of the impedance reaches a local minimum at this frequency.

Figure 4:
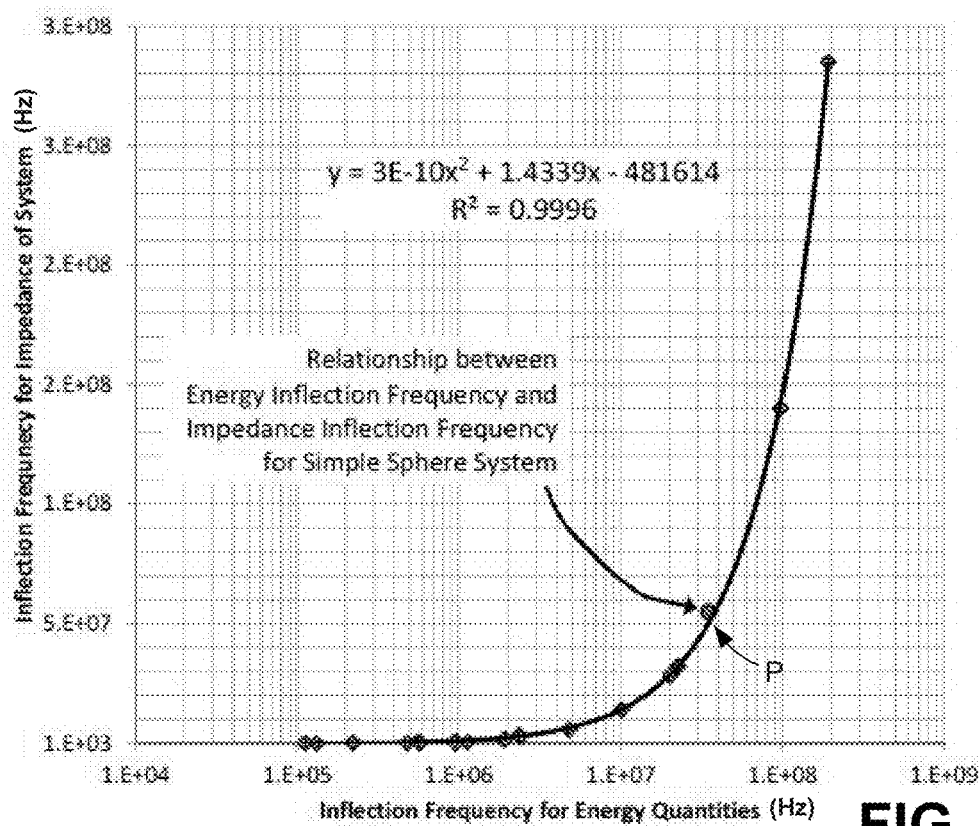
FIG. 4 is a graph that correlates inflection frequency for impedance of the system of FIG. 1 and inflection frequency for fields applied to the system.

Once the inflection frequency for the impedance of the system is known, it can be used to determine the inflection frequency for energy applied to the system, which may be a different frequency. The relationship between these two frequencies can be determined either empirically or through system modeling. Regardless, the relationship can be determined by correlating the inflection frequency of energy applied to the system and the inflection frequency for the impedance of the system. An example of such correlation is illustrated in the graph of FIG. 4. Along the x axis of this graph is the inflection frequency for energy applied to the system of FIG. 1 and along the y axis of the graph is the inflection frequency for the impedance of that system. In the example of FIGS. 2 and 3, the inflection frequency for the impedance of the system was $5.5 \times 10^7$ Hz and the inflection frequency for the energy applied to the system was $3.5 \times 10^7$ Hz. When intersection of these two values is plotted on the graph, a single data point P results. Further such points can be plotted as the electrical properties of the system are varied to construct a curve that correlates the inflection frequency for the impedance of the system with the inflection frequency for energy applied to the system. In this example, the curve can be mathematically defined as a second-order polynomial equation, which is identified in FIG. 4.

Once the relationship between the inflection frequency for the impedance of the system and the inflection frequency for energy applied to the system is known, it can be used to determine the excitation energy to generate an electromagnetic field to be applied to the system. For example, if a particular organ, such as the human heart, is modeled, the relationship between the inflection frequency for the impedance of the heart and the inflection frequency for energy applied to the heart can also be modeled. Once that relationship has been determined, the actual inflection frequency for the impedance of a patient's heart can be measured and the inflection frequency for the energy applied to the heart can be determined using the known relationship. With the knowledge of this inflection frequency, an excitation frequency above or below the inflection frequency can be selected in order to obtain a desired spatial distribution for the electromagnetic field.

Figure 5:
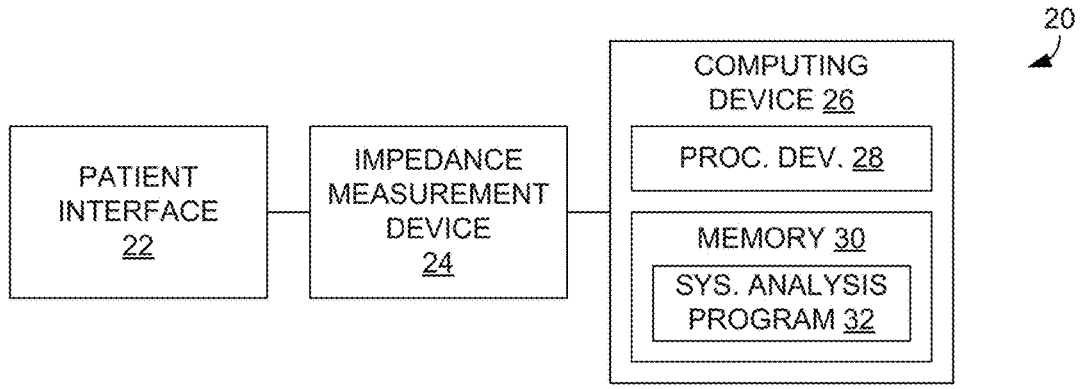
FIG. 5 is a block diagram of an embodiment of a system for controlling the spatial distribution of an electric field.
Figure 6:
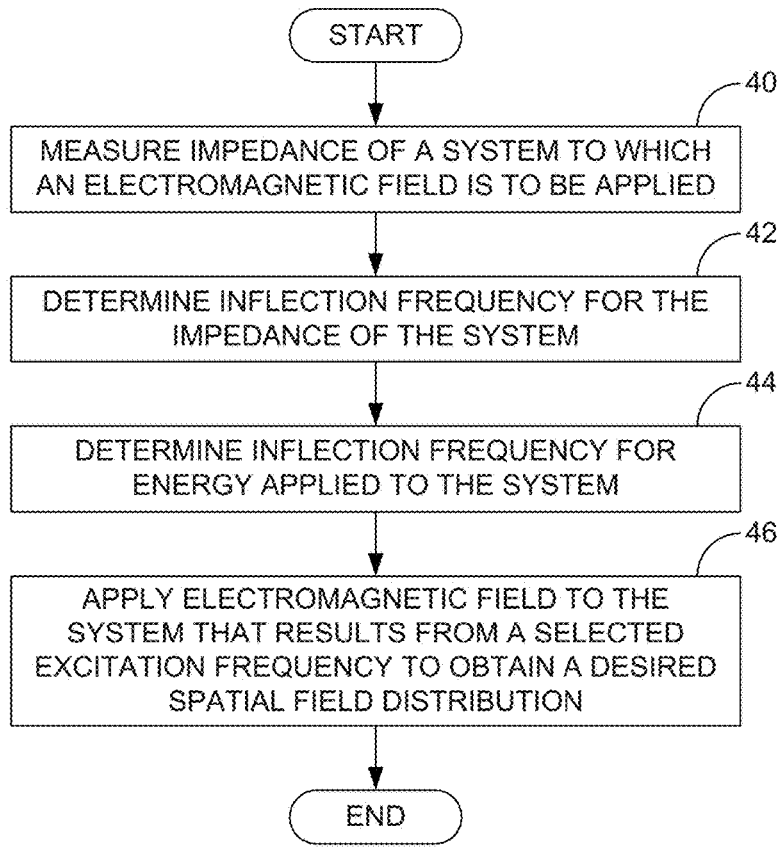
FIG. 6 is a flow diagram of an embodiment of a method for controlling the spatial distribution of an electric field.

FIGS. 5 and 6 illustrate an example apparatus and method, respectively, for controlling the spatial distribution of an electromagnetic field. Beginning with FIG. 5, shown is a block diagram of a system 20 that generally comprises a patient interface 22, an impedance measurement device 24 that is connected to the patient interface, and a computing device 26 that is connected to the impedance measurement device. The patient interface 22 can comprise any components that interface with the patient and can be used to apply electromagnetic excitation to part of the patient's body and receive signals that can be used to determine the impedance of that part of the body relative to various excitation frequencies. By way of example, these components can comprise one or more of electrodes, waveguides, antennas, and coils.

The impedance measurement device 24 can be configured to generate the electromagnetic energy applied by the patient interface 22 and receive the signals from the patient interface that are used to determine the impedance. In some embodiments, the impedance measurement device 24 comprises an impedance spectrometer that is configured to measure the dielectric properties of a medium as a function of excitation frequency.

The computing device 26 comprises a processing device 28 and memory 30 (a non-transitory computer-readable medium) that stores a system analysis program 32. The program 32 comprises logic that is configured to receive the impedance measurements from the impedance measurement device, determine the inflection frequency of the impedance of the system under evaluation (e.g., a part of a patient), and correlate that frequency to the inflection frequency for energy applied to the system.

While the impedance measurement device 24 and the computing device 26 have been illustrated as comprising independent components, it is noted that their respective functionalities can be performed by a single integrated device that is designed to assist users in selecting an excitation frequency to achieve a particular electromagnetic field distribution. Moreover, it is noted that the impedance measurement device 24, or the device that combines the functionality of that device and the computing device 26, can in some embodiments also be used to apply a voltage or current at a selected excitation frequency that is either above or below the determined inflection frequency to the system for the purpose of generating an electromagnetic field having a desired spatial distribution.

FIG. 6 illustrates an example method for controlling an electromagnetic field that can, at least in part, be performed by the system analysis program 32 identified in FIG. 5. Beginning with block 40 of FIG. 6, an impedance of a system to which an electromagnetic field is to be applied is measured. As indicated above, the system can comprise a particular part of a patient's body. For instance, the system can, in some cases, comprise a patient's organ or a part of a patient's organ. As described above, both the real and imaginary components of the system impedance can be measured as an excitation frequency of a voltage or current that is applied to the system is varied, for instance, from a low value to a high value. An example of such measurement is illustrated in FIG. 3, which was described above.

Next, with reference to block 42, the inflection frequency for the impedance of the system is determined. As described above, this inflection frequency can be determined by identifying an inflection point (i.e., change of slope) of the real component of the impedance, a local minimum of the imaginary component of the impedance, or both. Notably, it is possible for there to be multiple inflection frequencies for the impedance of the system. The inflection frequency or frequencies can either be measured or modeled, depending upon the situation.

With reference to block 44, the inflection frequency for energy applied to the system can be determined based upon the determined inflection frequency for the impedance of the system. As described above, the inflection frequency for energy applied to the system can be determined by correlating the determined inflection frequency for the impedance of the system with the inflection frequency for energy applied to the system using the known relationship between the two frequencies. FIG. 4 illustrates one such relationship, which can be expressed in graphical and/or mathematical form. With such a relationship, any measured or modeled inflection frequency for the impedance of the system can be used to determine the excitation frequency below which a first spatial distribution of an electromagnetic field will occur and above which a second spatial distribution of an electromagnetic field will occur.

When the inflection frequency for energy applied to the system is communicated to a user, the user can select excitation frequency, and therefore spatial distribution, that is most appropriate for the particular situation. Once this selection has been made, an electromagnetic field that results from a selected excitation frequency can be applied to the system to obtain a desired spatial distribution for the field, as indicated in block 46. In some embodiments, the excitation frequency can be below the inflection frequency for energy applied to the system. In other embodiments, the excitation frequency can be above the inflection frequency for energy applied to the system. In still other embodiments, the excitation frequency can be equal to the inflection frequency for energy applied to the system. It is further noted that more than one excitation frequency can be used. For example, excitation frequencies both above and below the inflection frequency for energy applied to the system can be used, either simultaneously or in an alternating fashion. In this manner, the spatial distribution can be custom tailored to achieve a particular outcome.

Figure 7:
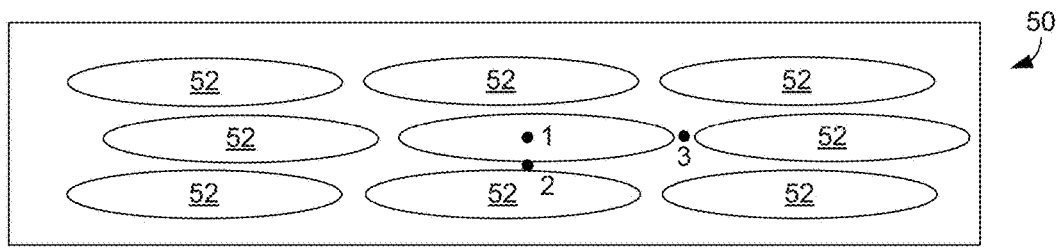
FIG. 7 is a schematic diagram of heart tissue to which an electric field is to be applied.

FIGS. 7-25 illustrate examples in which the above-described method can be applied. Beginning with FIG. 7, illustrated is a representation of section of heart tissue 50 that comprises multiple muscle cells 52. The size of each cell 52 is approximately 120 µm×20 µm×20 µm. Electric energy can be applied to the tissue 50 using a pacemaker or defibrillator. Point 1 shown in the figure is inside a myocyte. Point 2 is outside a cell 52 and in the path of an applied field. Point 3 is also in the extracellular space, but on one side of the cell 52 with respect to the direction of the applied field.

Figure 8:
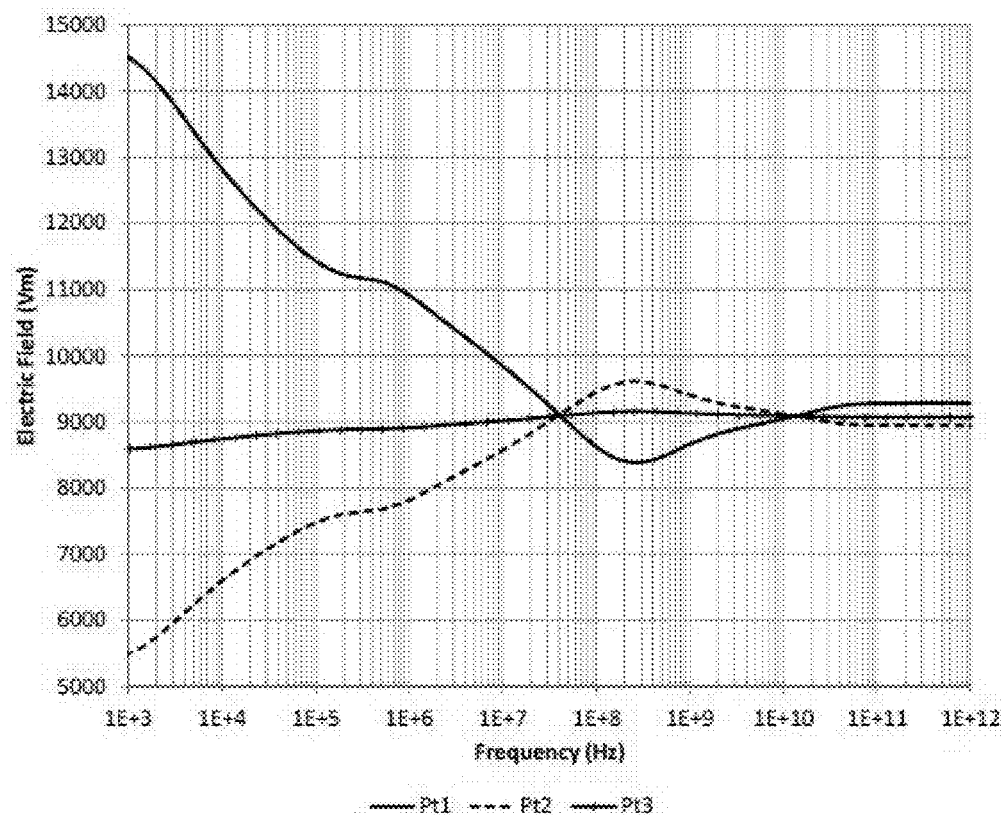
FIG. 8 is a graph that plots electric field intensity versus frequency at three different points in the heart tissue of FIG. 7.

FIG. 8 shows the electric field intensity at each of the three points within heart tissue 50. As indicated in this figure, an inflection frequency for energy applied to the heart tissue 50 occurs at $3 \times 10^7$ Hz where the three curves for the points intersect. Applied frequency components above this frequency will result in electric fields having the following relative intensities: Point 2>Point 3>Point 1. Excitations below this frequency will result in electric fields having the following relative intensities: Point 1>Point 3>Point 2. A combination of frequency excitations will lead to distributions of energy that have a cumulative effect resulting in a distribution of energy throughout the tissue.

Low-pass, high-pass, or band-pass signal filters can be used to attain different electric field distributions within the heart tissue 50. For example, if most of the applied electric field effect is desired within the cells (Point 1), then a low-pass filter with a cutoff frequency of 40 MHz can be applied. If the effect outside the cells (Points 2 and 3) is to be maximized, then a band-pass filter or a combination of low-pass and high-pass filters can be used so that frequencies below 40 MHz and 10 GHz are attenuated.

In another example using the geometry shown in FIG. 7, it is possible to equalize the exposure that Points 2 and 3 receive. To achieve this, the inflection frequency, which occurs at the point where the curve representing the values for electric field intensity for Point 2 meets with the curve for Point 3, can be used as the excitation frequency. At this frequency, both points are exposed to the same electric field intensity. Applying the excitation at this frequency will yield equalization of the effect at both points. Additionally, a combination of excitation frequencies, for example, at 10 MHz ($1\times10^7$ Hz) and at 100 MHz ($1\times10^7$ Hz), will yield the same effect.

Figure 9:
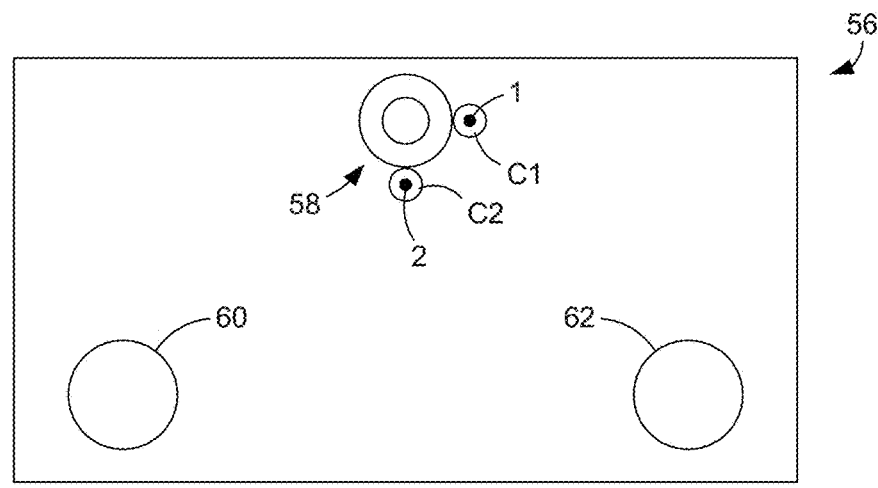
FIG. 9 is a schematic diagram of kidney tumor tissue to which an electric field is to be applied.
Figure 10:
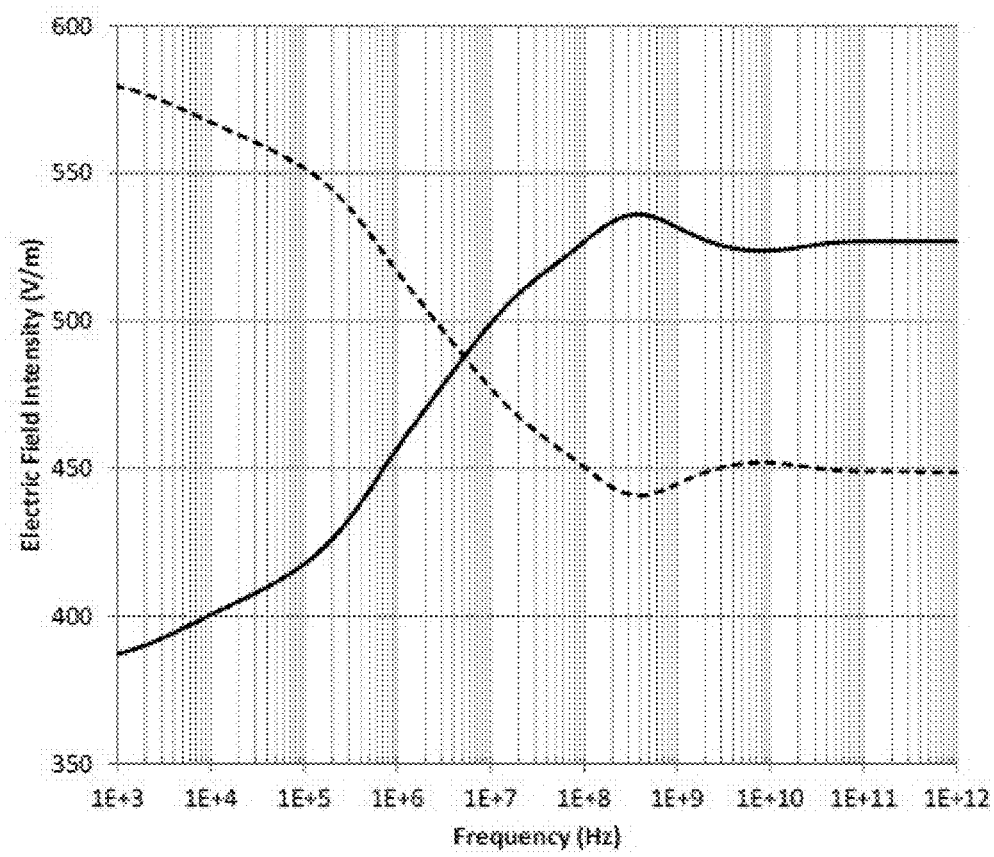
FIG. 10 is a graph that plots electric field intensity versus frequency at two different points in the kidney tumor tissue of FIG. 9.

FIG. 9 shows a representation of kidney tumor tissue 56 through which passes a blood vessel 58. Positioned in the tissue 56 near the blood vessel 58 are electrodes 60 and 62 of a bipolar ablation device. Two points, Points 1 and 2, are identified in the figure for which electric field intensities are to be determined. Volumes C1 and C2 encapsulate Point 1 and Point 2, respectively. In the graph of FIG. 10, the solid line corresponds to the electric field intensity at Point 1, which is below the blood vessel 58. The dashed line corresponds to the electric field intensity at Point 2, which is to one side of the blood vessel 58. Frequency components of applied energy above $3.5\times10^6$ Hz (where both curves intersect) will result in greater electric field on the sides of the blood vessel 58. Frequency components below that frequency will result in greater electric fields above and below the blood vessel 58. It is possible to combine frequency contributions within one or more excitation pulses or waves to generate a cumulative effect of applied energy to the kidney tumor tissue 56. It is also possible to use similar excitation combinations to deposit more or less energy on the blood vessel 58 in comparison with the kidney tumor tissue 56.

As an example, two frequencies, one above (10 MHz) and one below (1 MHz) the inflection frequency, can be selected to apply the electric fields using the electrodes 60, 62 inserted in the tissue 56. The graph in FIG. 11 shows the values for energy absorption in the volumes C1 (solid line) and C2 (dashed line) for a range of frequencies.

The total energy distributed can be calculated using the following formula:

$$E_{TOTAL}(\text{spectrum})=E_{C1}(1\text{ MHz})+E_{C1}(10\text{ MHz})+E_{C2}(1\text{ MHz})\pm E_{C2}(10\text{ MHz}) \quad \text{(Equation 1)}$$

Figure 11:
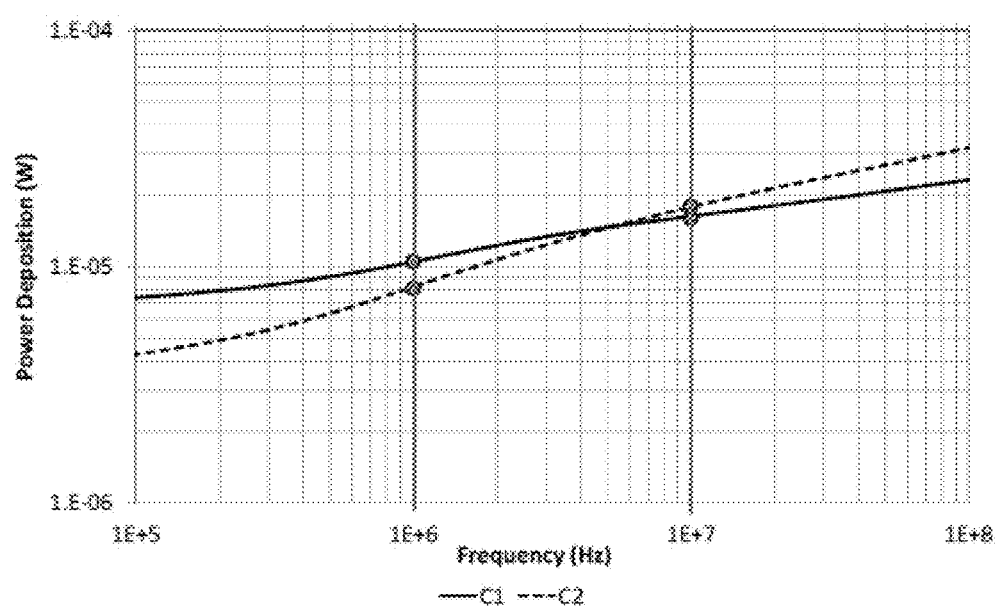
FIG. 11 is a graph that plots power deposition versus frequency at two different volumes in the kidney tumor tissue of FIG. 9.
Figure 12A:
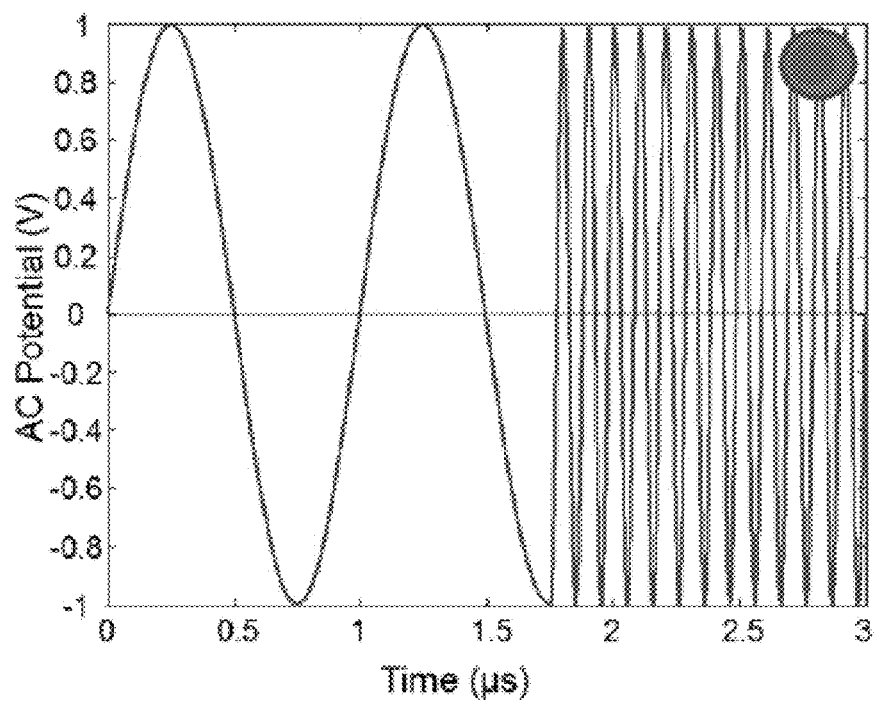
FIGS. 12A and 12B are graphs that illustrate example waveforms that can be used to generate an electric field to be applied to the kidney tumor tissue of FIG. 9.

The following equation is solved for the values in FIG. 11.

$$E_{C1}(1\text{ MHz})\pm E_{C1}(10\text{ MHz})=E_{C2}(1\text{ MHz})+E_{C2}(10\text{ MHz}) \quad \text{(Equation 2)}$$

indicating that the magnitude of the signal at 1 MHz must contain 45.5% of the power and the signal at 10 MHz must contain 54.5% of the power. The same power deposition at C1 and C2 can be generated in various ways. In a first example, two waveforms, one with a frequency of 1 MHz and a subsequent waveform with 10 MHz, can be used. An example of this is shown in FIG. 12A. To have the same energy absorption in both volumes, the 1 MHz signal needs to contain 45.5% and the 10 MHz needs to contain the 54.5% of the applied power. The two waveforms can be applied for the same duration, but the 1 MHz waveform is of lower magnitude.

In a second example, two waveforms, one with a frequency of 1 MHz and a subsequent waveform with 10 MHz, can be used. To have the same energy absorption in both volumes, the 1 MHz signal needs to contain 45.5% and the 10 MHz signal needs to contain the 54.5% of the applied power. The two waveforms have the same magnitude, but the 1 MHz waveform is applied for a shorter time so that it reaches only 45.5% of the total power applied.

Figure 12B:
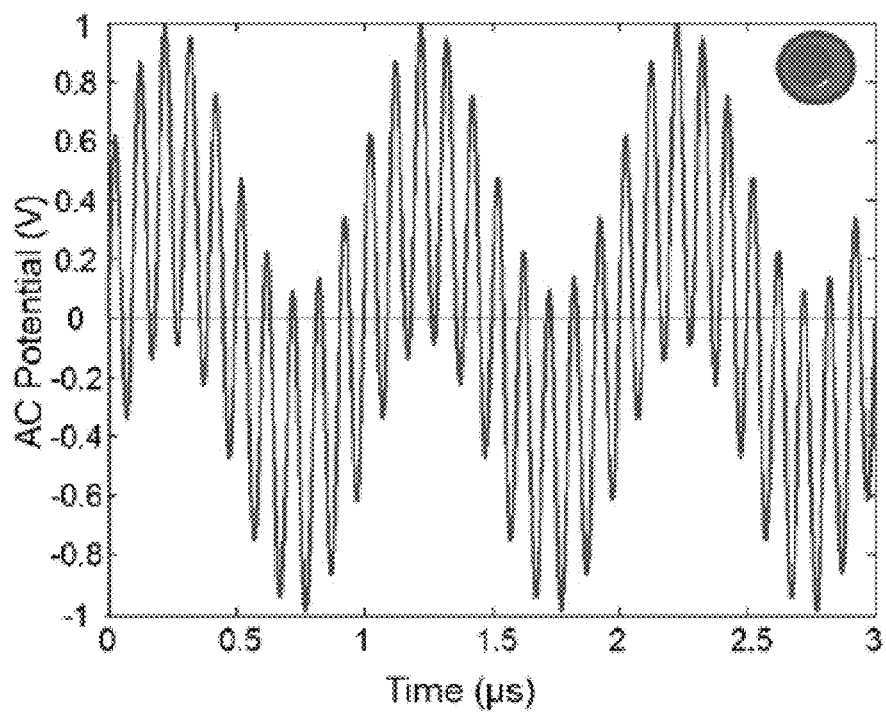

In a third example, a single waveform or pulse containing both frequencies can be composed by applying a Fourier Transform. An example of this is shown in FIG. 12B. Again, the 1 MHz signal contains 45.5% of the power and the 10 MHz contains 54.5% of the power.

More complex waveforms having multiple frequencies can be applied to get the same result as described above, as long as their power distribution attains the same spatial distribution effect.

Figure 13:
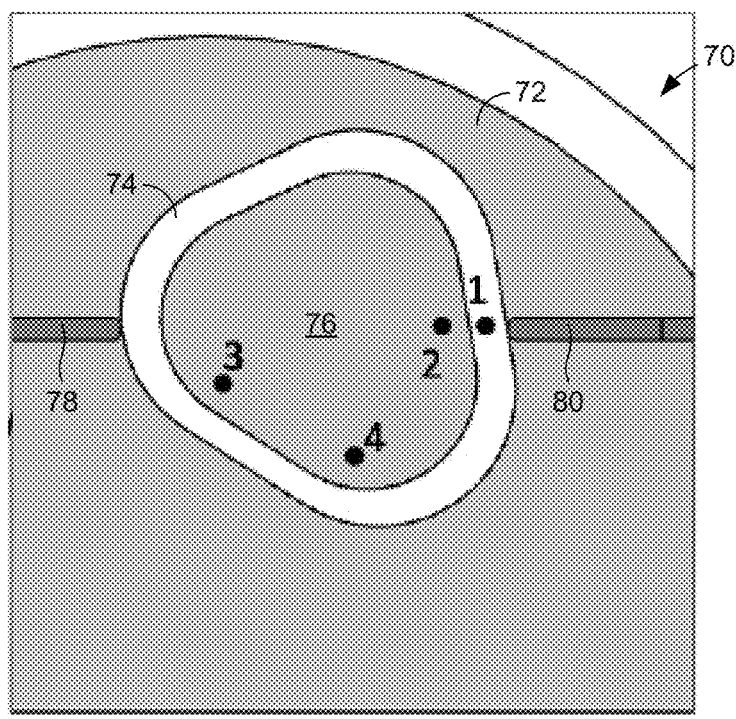
FIG. 13 is a schematic diagram of tissues of a human leg to which an electric field is to be applied.

FIG. 13 illustrates an axial slice of a human leg 70 showing muscle tissue 72, bone 74, and bone marrow 76 of the leg. Four different points are identified for which electric fields are to be calculated in the frequency domain. Point 1 is inside the bone 74, while Points 2-4 are inside the bone marrow 76. Two electrodes 78 and 80 of a bipolar ablation device are shown inserted in the leg 70 and are placed to the immediate left and the right of the bone 74. The electrodes 78, 80 can be used for both impedance measurement and applying energy by generating a potential difference between the two electrodes.

Figure 14:
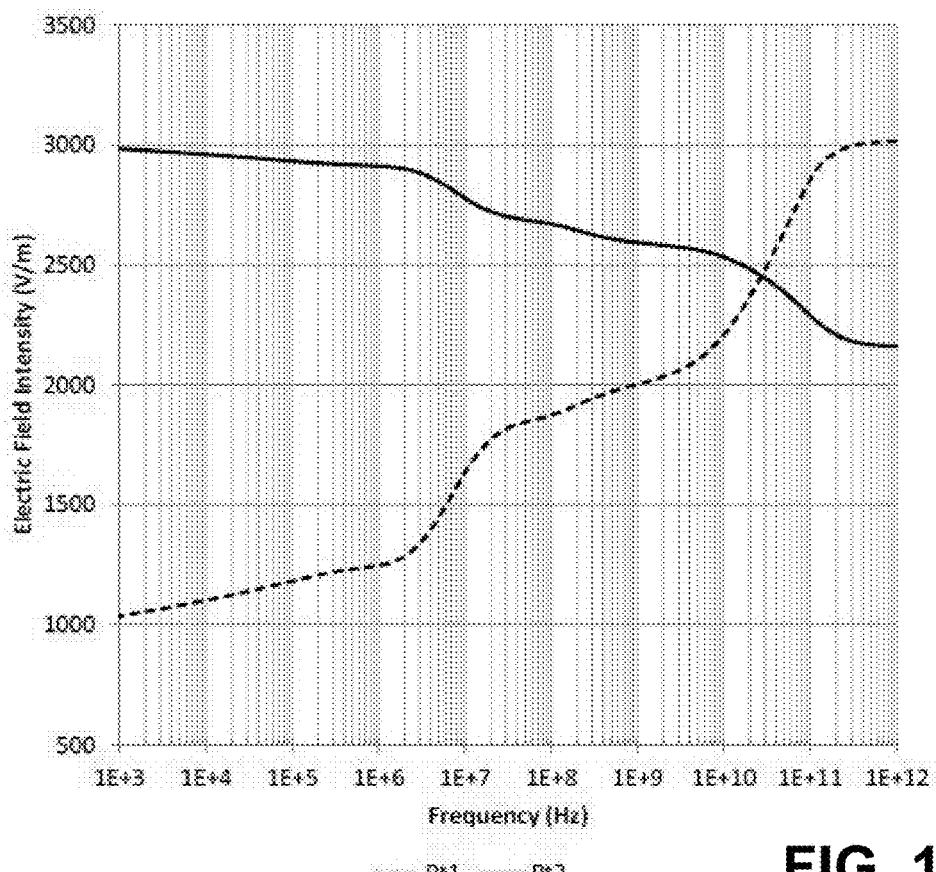
FIG. 14 is a graph that plots electric field intensity versus frequency at first and second points in the tissue of FIG. 13.
Figure 15:
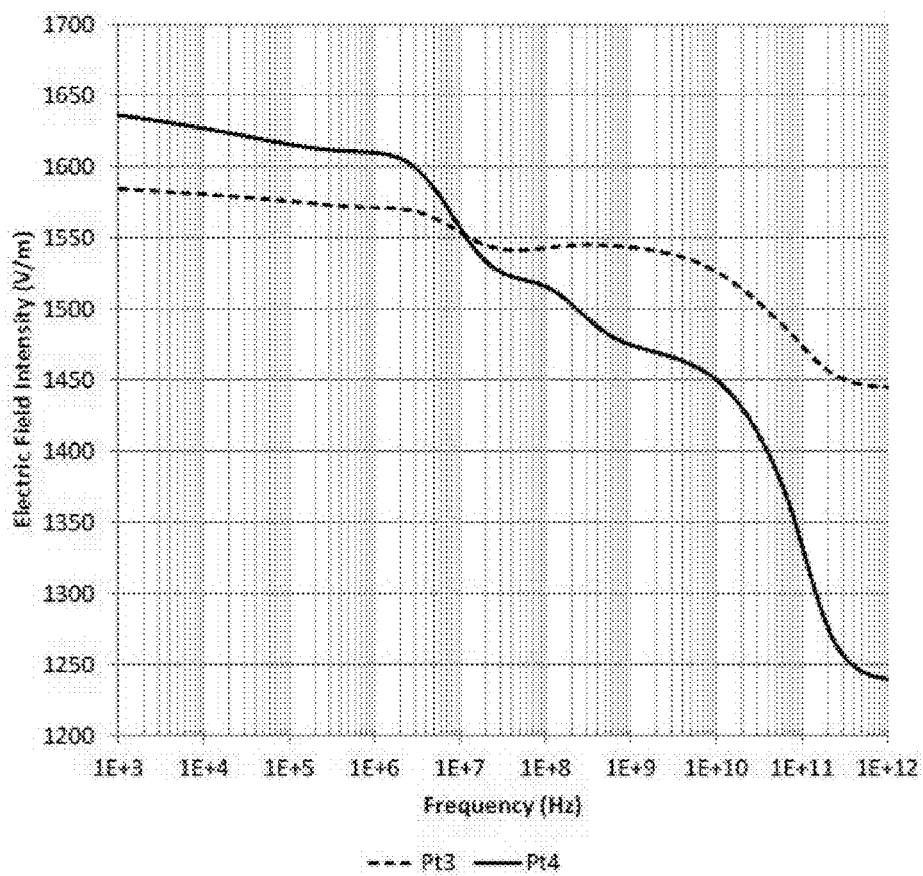
FIG. 15 is a graph that plots electric field intensity versus frequency at third and fourth points in the tissue of FIG. 13.

When an electric waveform is applied using the electrodes 78, 80, a distribution of fields develops in the different tissues. FIG. 14 shows the electric field intensities for Points 1 and 2, and FIG. 15 shows the electric field intensities for Points 3 and 4. In FIG. 14, the solid line corresponds to the electric field intensity at a Point 1 and the dashed line corresponds to the electric field intensity at Point 2. In FIG. 15, the solid line corresponds to the electric field intensity at a Point 4 and the dashed line corresponds to the electric field intensity at Point 3. With reference to FIG. 14, frequency components of applied energy above $2.5\times10^{10}$ Hz where both curves intersect (the inflection frequency) will result in greater electric field and energy deposited at the cortical bone 74. Frequency components below that frequency will result in greater electric field intensity and energy deposited within the bone marrow 76. It is possible to preferentially use excitation frequencies below the critical frequency of the electric field.

With reference to FIG. 15, frequency components of applied energy above $1.3\times10^7$ Hz where both curves intersect (the inflection frequency) will result in greater electric field and energy deposited at Point 3. Frequency components below that frequency will result in greater electric field intensity and energy deposited at Point 4. It is possible to preferentially use excitation frequencies below the inflection frequency of the electric field.

A further example involving the leg can be one of electroporation in which the electrodes 60, 62 are used to drive therapeutic molecules into the tissue for purposes of drug or gene delivery. In such a case, a set of two frequencies, 2.5 MHz and 20 MHz, can be chosen and the amount of excitation at each frequency necessary so that each point is exposed to the same electric field intensity can be calculated by solving the following equations:

$$X\cdot E_{P2}(2.5\text{ MHz})+Y\cdot E_{P2}(20\text{ MHz})=X\cdot E_{P3}(2.5\text{ MHz})\pm Y\cdot E_{P3}(20\text{ MHz}) \quad \text{(Equation 3)}$$

and $$X+Y=100\% \quad \text{(Equation 4)}$$

where $E_{P2}$ (2.5 MHz) and $E_{P3}$ (2.5 MHz) are the electric field intensity at Points 2 and 3 when an excitation wave of 2.5 MHz is applied, $E_{P2}$ (20 MHz) and $E_{P3}$ (20 MHz) are the electric field intensity at Points 2 and 3 when an excitation wave of 20 MHz is applied, and X and Y are the necessary excitation waveforms at 2.5 MHz and 20 MHz respectively.

For this example, solving the equations for these two points in the geometry at the two frequencies yields values of 24% for X and 76% for Y. In view of these results, an equivalent electric field intensity at Points 1 and 2 can be obtained in several ways. In a first example, two waveforms, one with a frequency of 2.5 MHz and a subsequent waveform with 20 MHz, can be used. To have the same electric field intensity in both points, the 2.5 MHz signal needs to contain 24% and the 20 MHz needs to contain the 76% of the applied field. The two waveforms can be applied for the same duration, but the 1 MHz waveform is of lower magnitude. Alternatively, two waveforms can have the same magnitude, but the 2.5 MHz waveform is applied for a shorter time so that it reaches only 24% of the total field applied.

In a further example, a single waveform or pulse containing both frequencies can be composed by applying a Fourier Transform. The 2.4 MHz signal contains 24% of the field and the 20 MHz contains 76% of the field.

More complex waveforms, with multiple frequencies, can be applied to obtain the same result as above, as long as their field distribution attains the same spatial distribution effect. In addition, a more complex example using the same principles could be built to homogenize the distribution of field intensities in a volume. Increasing complexity could be used to obtain an arbitrary distribution of fields.

Figure 16:
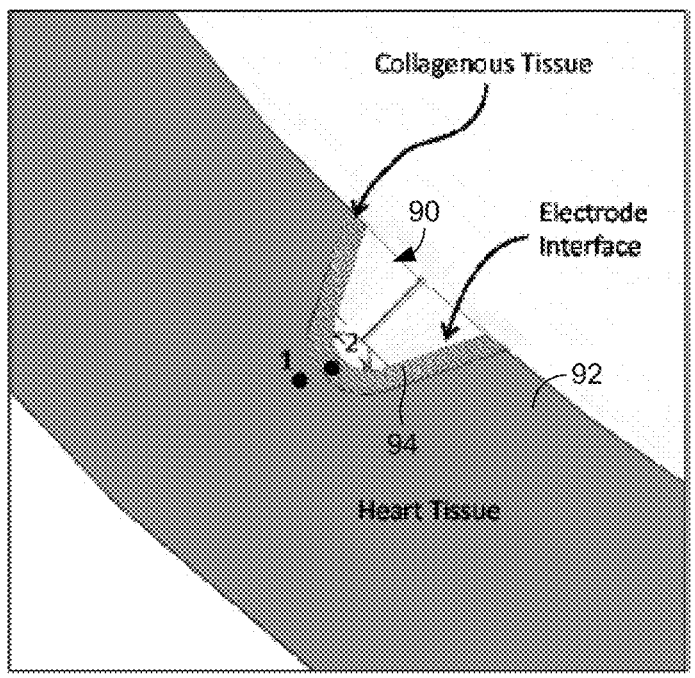
FIG. 16 is a schematic diagram of heart tissue to which an electric field is to be applied.

With reference next to FIG. 16, illustrated is a representation of an electrical lead 90 embedded in the right ventricle 92 of a heart for the purpose of exciting heart tissue. As shown in the figure, collagenous tissue 94 has formed in the heart tissue in the immediate vicinity of the lead because of the presence of the lead 90 and the electrical stimulation applied with it. Point 1 identifies a location within the heart tissue close to the lead 90 and Point 2 identifies a location within the collagenous tissue 94.

Figure 17:
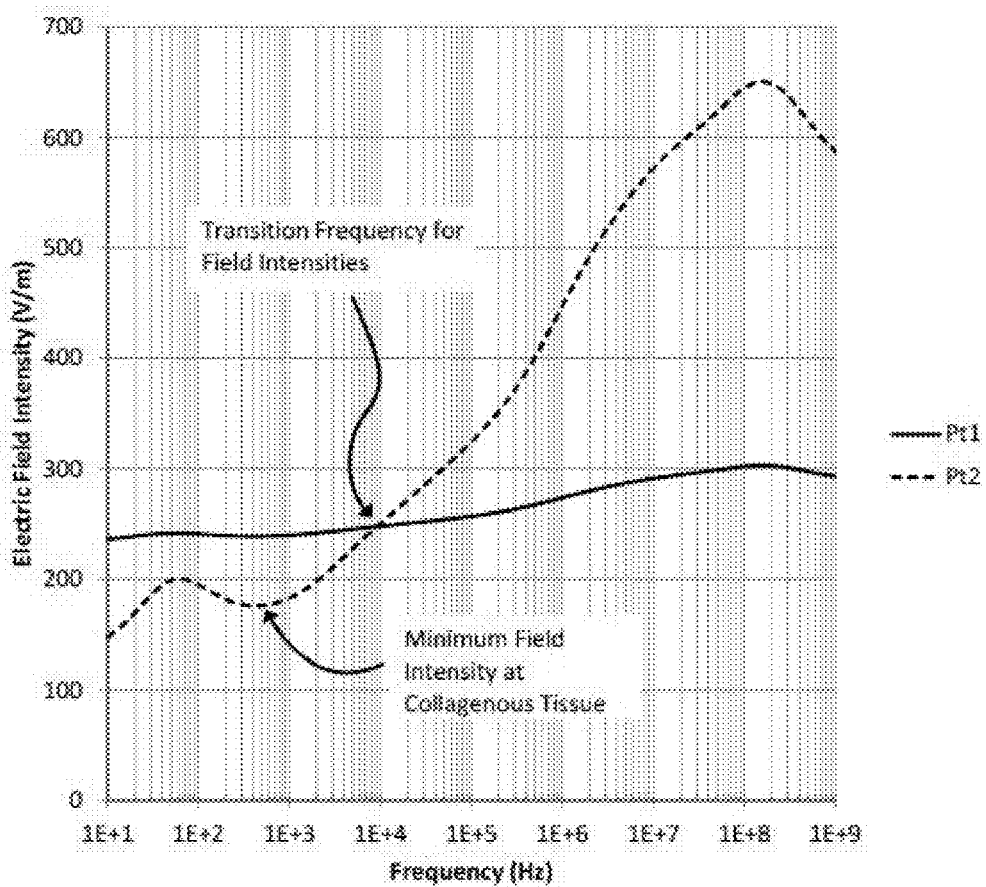
FIG. 17 is a graph that plots electric field intensity versus frequency at two different points in the heart tissue of FIG. 16.

FIG. 17 shows the electric field intensity at the two points. The solid line represents the electric field intensity at Point 1, while the dashed line represents the electric field intensity at Point 2. As is apparent from the figure, frequency components of the applied field above $8 \times 10^3$ Hz where both curves intersect (the inflection frequency) will result in greater electric field and energy deposited within the collagenous tissue 94, while frequency components below that frequency will result in greater electric field intensity and energy deposited within the heart tissue. It is possible to preferentially use excitation frequencies below the critical frequency of the electric field. Such frequency can be estimated from a critical frequency within impedance measurements that use the same electrode or additional electrodes.

Figure 18:
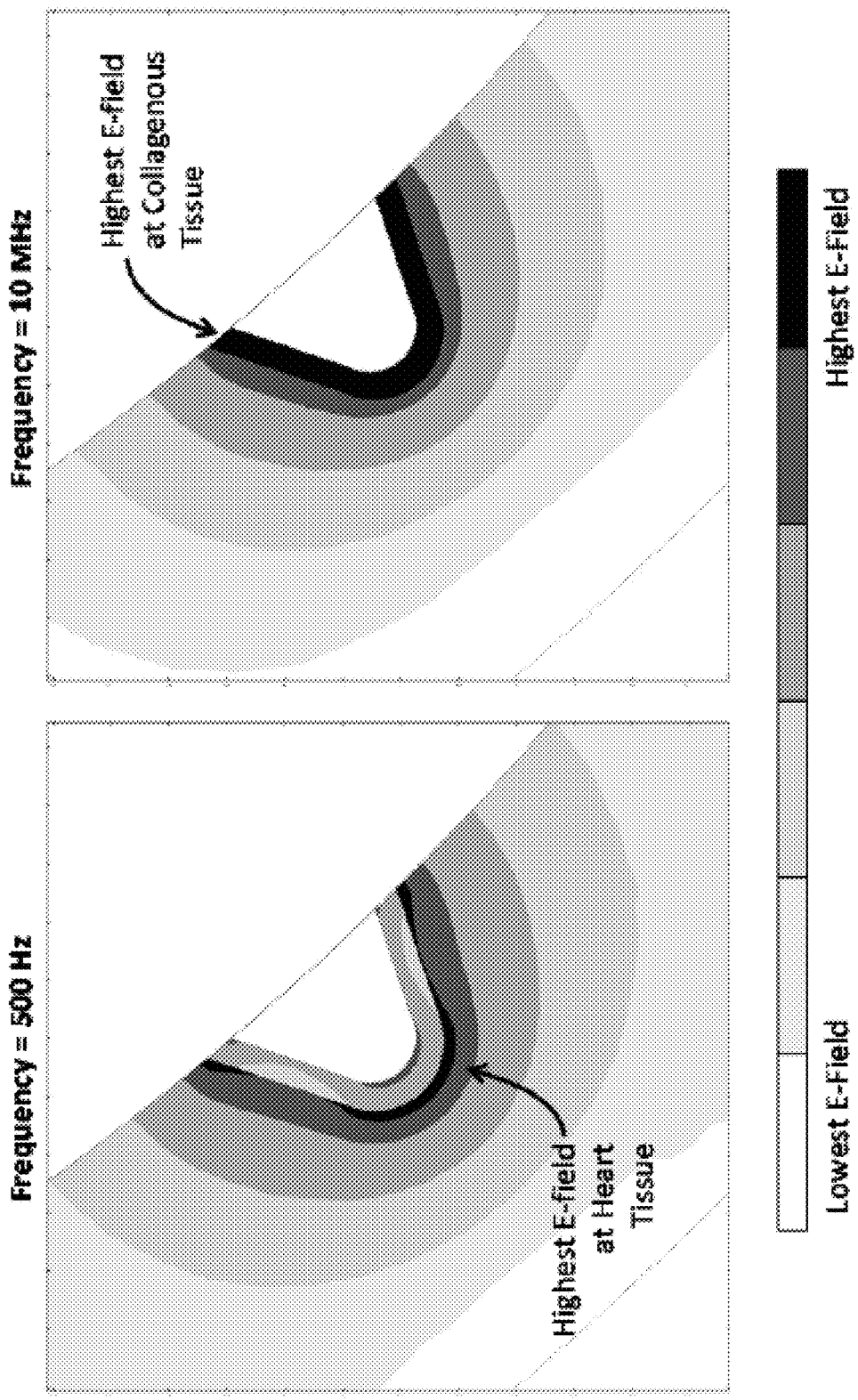
FIG. 18 includes graphs that plot the spatial distributions of electric field intensity that result from a 500 Hz and 10 MHz excitation frequency, respectively.
Figure 19:
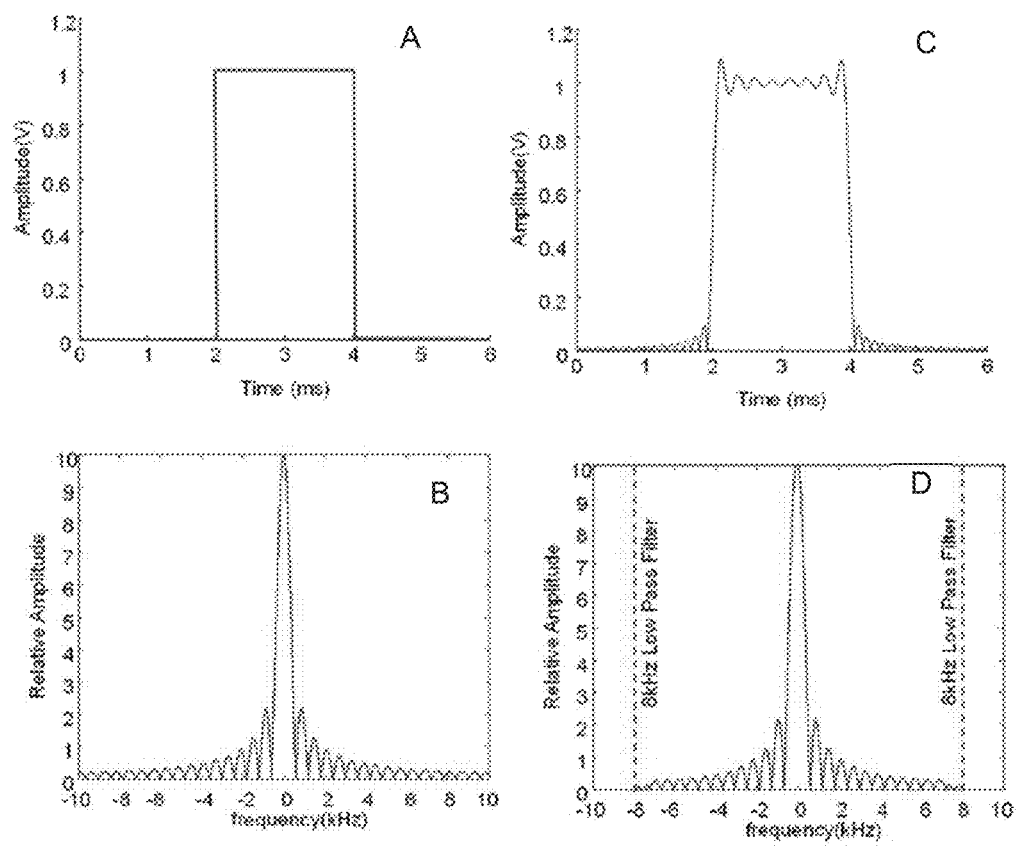
FIGS. 19A-19D are graphs that plot amplitude versus time and amplitude versus frequency of waveforms that can be used to generate an electric field to be applied to the heat tissue of FIG. 16.

FIG. 18 illustrates the spatial distributions of an electric field when an excitation of 500 Hz and 10 MHz are used, respectively. As indicated in this figure, an excitation of 500 Hz results in the highest field being located within the heart tissue, which an excitation frequency of 10 MHz results in the highest field being produced within the collagenous tissue 94.

FIGS. 19A-19D show waveforms that can be used in the example of FIG. 16. As shown in FIG. 19A, a 2 ms rectangular pulse can be chosen. FIG. 19B shows a sample of the frequency distribution for a perfect 2 ms pulse. To maintain most of the frequency components of a rectangular pulse under 8 kHz so that electric field intensity at the heart tissue is maximized, an 8 kHz low-pass filter can be applied in the frequency domain, as shown in FIG. 19D, which shows the resulting rectangular pulse in the time domain with the high frequencies removed. The application of pulses such as that shown in FIG. 19D will generate a predominantly higher electric field intensity in the heart tissue (Point 1 in FIG. 16) and minimal electric field intensity in the collagenous tissue (Point 2 in FIG. 16). Pacemaker and implantable defibrillator waveforms can be built and modified to include other important parameters but following the principles in this example. Furthermore, waveforms constructed using these principles can be used in the case external defibrillators, which do not have the collagenous encapsulation but have other tissues between the electrodes and the heart.

Figure 20:
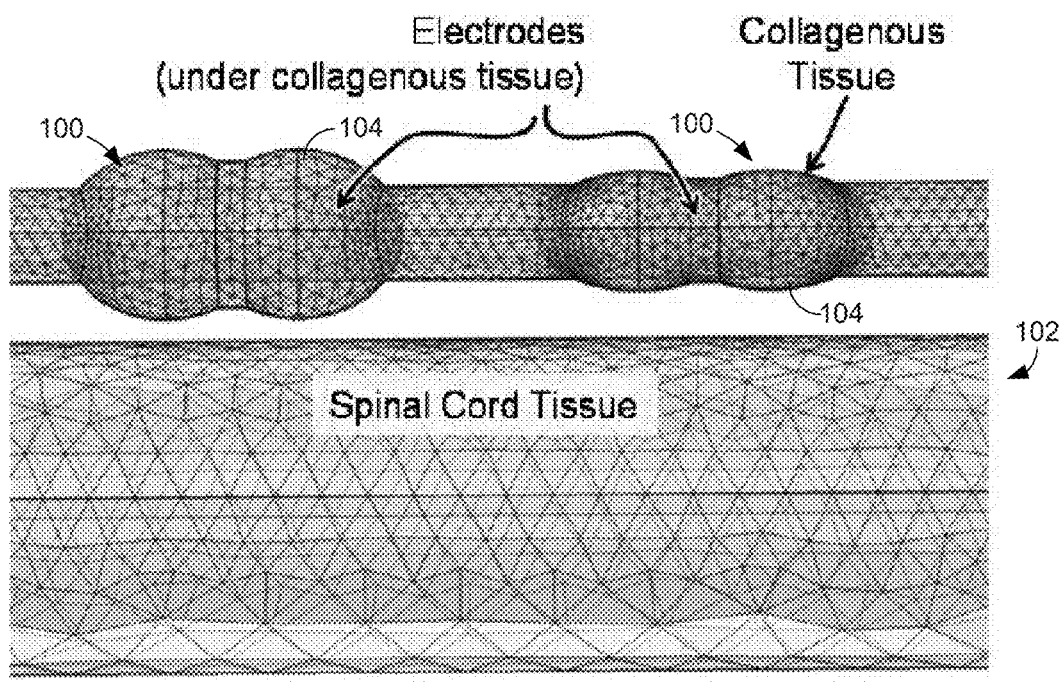
FIG. 20 is a schematic diagram of tissue near the spinal cord to which an electric field is to be applied.

Referring next to FIG. 20, illustrated are implanted electrodes 100 that are positioned near spinal cord tissue 102 to excite nervous tissues in neuromodulation applications, such as pain management. A common problem in such applications is collagenous encapsulation of the electrodes 100 in which case collagenous tissue 104 surrounds the electrodes. Such encapsulation creates the need for increased pulse power over time. In FIG. 20, Point 1 identifies a point within the collagenous tissue 104 and Points 2 and 3 identify points within the spinal cord tissue 102.

Figure 21:
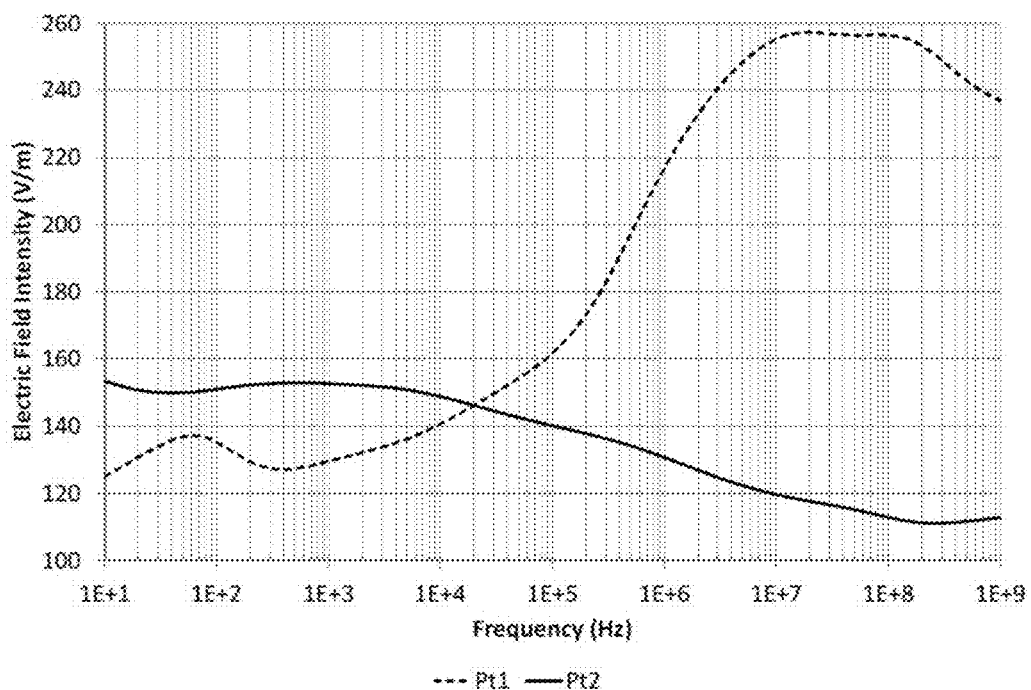
FIG. 21 is a graph that plots electric field intensity versus frequency at a first point and a second point in the tissue of FIG. 20.

FIG. 21 shows the electric field intensity for Points 1 and 2 across a range of frequencies. The inflection frequency components for which the excitation waveform creates a larger electric field intensity within the spine is below 20 MHz. This transition frequency can be experimentally determined using impedance spectroscopy or using computational models. Above this frequency, the electric field intensities are of greater magnitude at the collagenous encapsulation. To maximize the electric field intensity, the current, or the power at the spine tissue and minimize them at the site of the encapsulation, it is possible to apply an electronic filter to the waveform such that only frequency components below 20 MHz are used in the excitation waveform.

Figure 22:
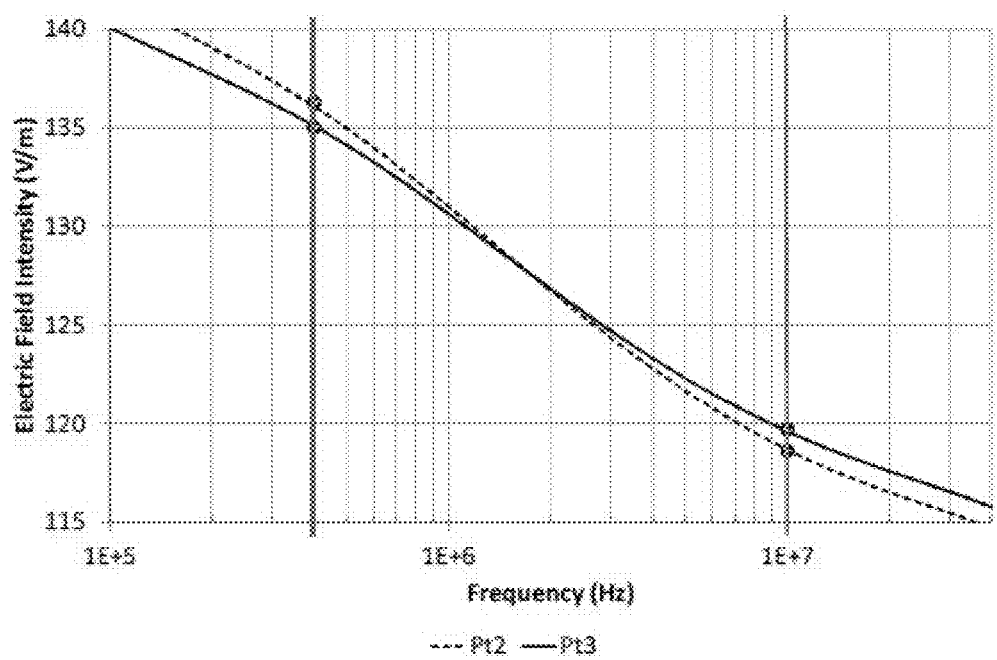
FIG. 22 is a graph that plots electric field intensity versus frequency at the second and a third point in the tissue of FIG. 20.

Another problem associated with tissue encapsulation can occur because of differential tissue encapsulation from electrode to electrode, making distribution of fields geometrically vary. For example, if Points 2 and 3 in FIG. 20 are to have the same electric field intensity (or also current intensity or power deposition), it can be challenging to achieve this result if the electrodes 100 are encapsulated to different degrees. FIG. 22 shows the values for electric field intensity at Points 2 and 3. For this specific case, the inflection frequency is at 1.5 MHz. Below this frequency, the electric field intensity at Point 2 is higher. Above this frequency, the electric field intensity at Point 3 is higher.

To achieve balanced electric field intensities at Points 2 and 3, it is possible to compose waveforms with components below and above the inflection frequency. A simple embodiment of such pulse can have only two frequency components. In this case, 400 kHz and 10 MHz are chosen. To achieve equal electric field intensity at Points 2 and 3, it is possible to solve the Equations 3 and 4 mentioned above for this case. For this specific case, waveforms with frequency components of the waveform at 45.8% at the low frequency (400 kHz) and 54.8% at the high frequency will yield balanced distribution at Points 2 and 3. This effect can be achieved in varied combinations of waveform frequency components, their magnitude, or the amount of length of the excitation in time.

Figure 23:
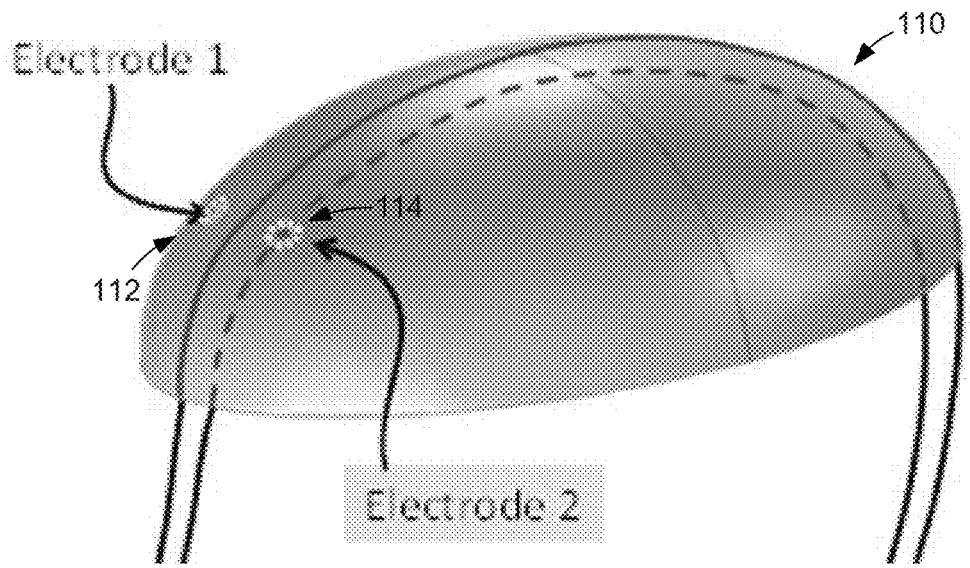
FIG. 23 is a schematic diagram of a human head to which an electric field is to be applied.
Figure 24:
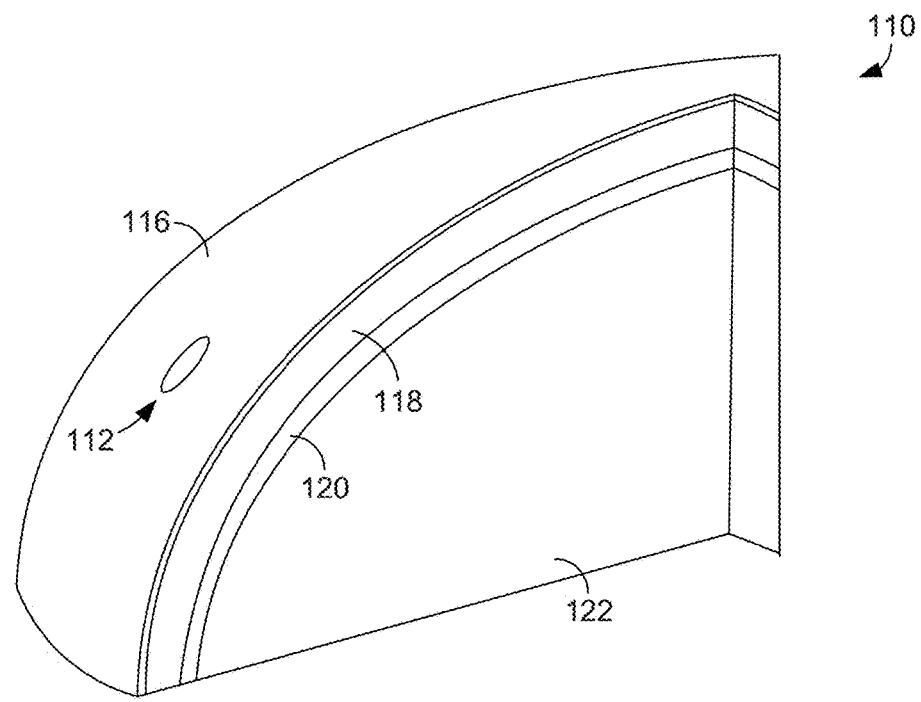
FIG. 24 is a detail view of the head of FIG. 23.

FIG. 23 shows a representation of the top of a head 110 to which has been applied two surface electrodes 112 and 114. FIG. 24 shows a detail view that identifies several tissue layers including skin 116, bone 118, cerebrospinal fluid 120, and brain tissue 122, which have different dielectric properties.

Figure 25:
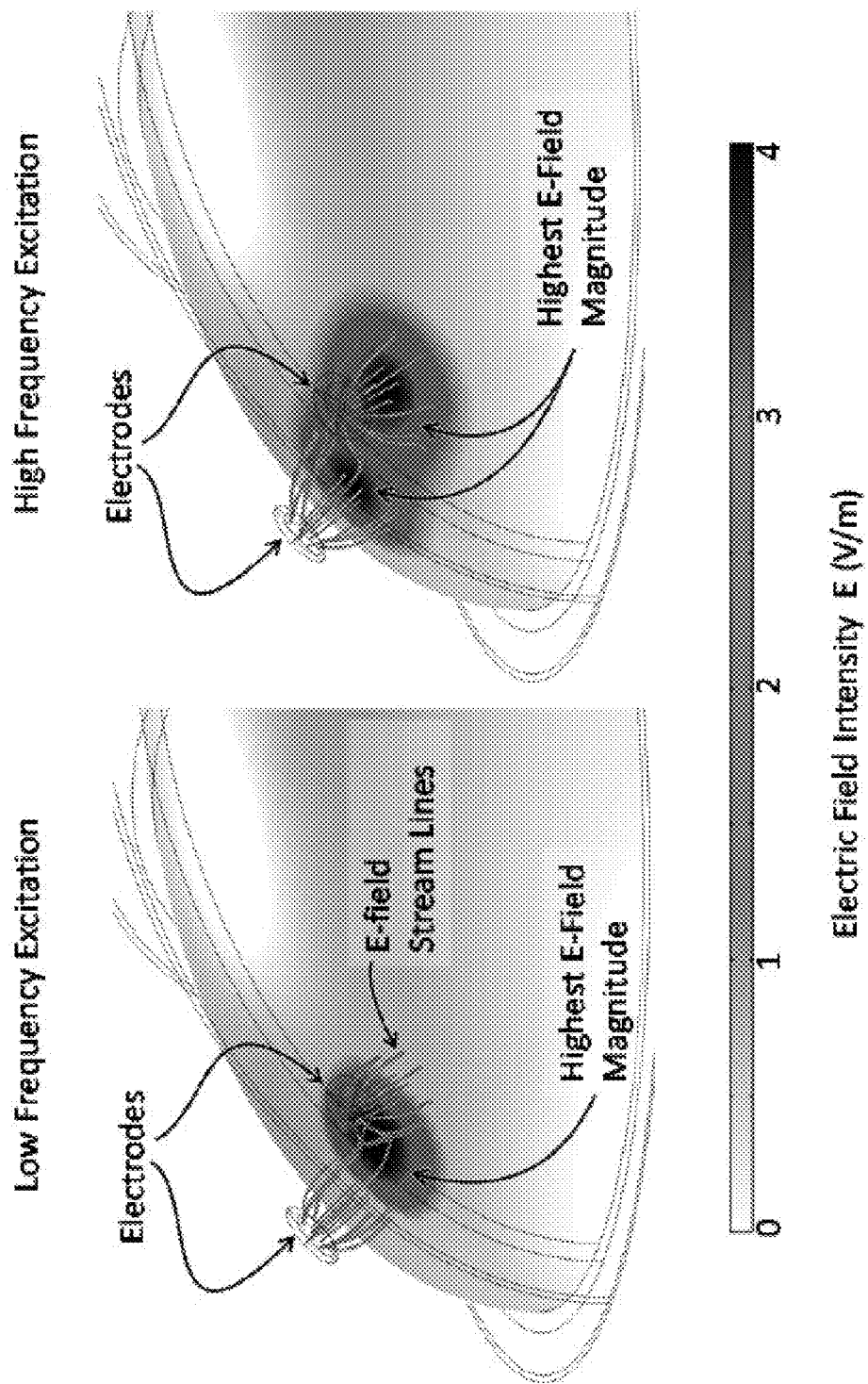
FIG. 25 includes electric field intensity surface maps that illustrate electric intensity for a low excitation frequency and a high excitation frequency, respectively.

FIG. 25 shows electric field intensity surface maps at the surface of the brain resulting from the application of a low excitation frequency and a high excitation frequency, respectively. While the excitation is applied at the skin using electrodes 112 and 114, the desired electric effects are at the surface or cortex of the brain. As with the previous examples, combinations of frequency components can be used in excitation waveforms to achieve different distributions. One, two, or more electrodes can be used with combinations of frequency components to achieve desired field effects at the cortex of the brain.

Although multiple example therapeutic applications have been identified in relation to FIGS. 7-25, it is noted that there are others. For example, the principles disclosed herein can be used in the context of electromagnetic fields for tissue regeneration, iontophoresis for drug delivery, treatment of hypothermia, electrosurgery applications for cutting, coagulation, desicating, or fulgurating tissues or any other application where energy in the electromagnetic spectrum needs to be delivered to biological tissues. Moreover, these principles can be used in measuring applications associated with electric impedance microscopy, lorentz force electric impedance spectroscopy, linear sweep voltammetry, potentiodynamic electric impedance spectroscopy, and polarization resistance-based methods.

The invention claimed is:

1. A method for controlling the spatial distribution of an electromagnetic field in a system, the method comprising:
   determining an inflection frequency for energy applied to the system below which a first spatial field distribution results and above which a second spatial field distribution results;
   selecting an excitation frequency to be used to generate an electromagnetic field to be applied to the system based upon the determined inflection frequency; and
   applying an electromagnetic field to the system generated using the selected excitation frequency.

2. The method of claim 1, wherein determining an inflection frequency for energy applied to the system comprises determining an inflection frequency for the impedance of the system.

3. The method of claim 2, wherein determining an inflection frequency for the impedance of the system comprises determining the impedance of the system across multiple frequencies.

4. The method of claim 3, wherein determining the impedance comprises measuring the impedance across multiple frequencies.

5. The method of claim 3, wherein determining the impedance comprises modeling the impedance across multiple frequencies.

6. The method of claim 3, wherein determining the impedance comprises determining one or both of real and imaginary components of the impedance of the system across the multiple frequencies.

7. The method of claim 6, wherein determining the inflection frequency for the impedance of the system further comprises identifying a frequency at which an inflection point occurs for the real component of the impedance.

8. The method of claim 6, wherein determining the inflection frequency for the impedance of the system further comprises identifying a frequency at which a local minimum occurs for the imaginary component of the impedance.

9. The method of claim 2, wherein determining an inflection frequency for energy applied to the system further comprises correlating the inflection frequency for the impedance of the system to the inflection frequency for energy applied to the system using a mathematical relation.

10. The method of claim 9, wherein the mathematical relation is based upon measured spatial field distributions.

11. The method of claim 9, wherein the mathematical relation is based upon modeled spatial field distributions.

12. The method of claim 1, wherein applying an electromagnetic field comprises applying an electromagnetic field generated using an excitation frequency below the inflection frequency for energy applied to the system.

13. The method of claim 1, wherein applying an electromagnetic field comprises applying an electromagnetic field generated using an excitation frequency above the inflection frequency for energy applied to the system.

14. The method of claim 1, wherein applying an electromagnetic field comprises applying an electromagnetic field generated using an excitation frequency at the inflection frequency for energy applied to the system.

15. A system for controlling the spatial distribution of an electromagnetic field applied to media, the system comprising:
   means for determining an inflection frequency for energy applied to the media below which a first spatial field distribution results and above which a second spatial field distribution results; and
   means for applying an electromagnetic field to the media generated using an excitation frequency that was selected based upon the determined inflection frequency.

16. The system of claim 15, wherein the means for determining comprise a processing device that executes a system analysis program configured to determine an inflection frequency for impedance of the system.

17. The system of claim 16, wherein the means for determining further comprise an impedance measurement device configured to measure the impedance of the media across multiple frequencies.

18. The system of claim 17, wherein the impedance measurement device is configured to measure real and imaginary components of the impedance of the media across the multiple frequencies.

19. The system of claim 18, wherein the system analysis program is configured to identify a frequency at which an inflection point occurs for the real component of the impedance.

20. The system of claim 18, wherein the system analysis program is configured to identify a frequency at which a local minimum occurs for the imaginary component of the impedance.

21. The system of claim 18, wherein the system analysis program is further configured to correlate the measured inflection frequency for the impedance of the system to the inflection frequency for energy applied to the system using a mathematical relation.

22. A non-transitory computer-readable medium that stores a system analysis program configured to facilitate control over the spatial distribution of an electromagnetic field in a system, the program comprising:
   logic configured to determine an inflection frequency for the impedance of a system;
   logic configured to determine an inflection frequency for energy applied to the system based upon the determined inflection frequency for the impedance of the system, wherein a frequency of an electromagnetic field to be applied to the system can be selected relative to the determined inflection frequency for energy applied to the system to alter the distribution of the electromagnetic field within the system and therefore be focused on a target within the system.

23. The computer-readable medium of claim 22, wherein the logic configured to determine an inflection frequency for the impedance of the system is configured to receive impedance measurements for the system across multiple frequencies and determine the inflection frequency for the impedance of the system based the impedance measurements.

24. The computer-readable medium of claim 23, wherein the logic configured to determine an inflection frequency for the impedance of the system is configured to identify one or both of a frequency at which an inflection point occurs for a real component of the impedance and a frequency at which a local minimum occurs for an imaginary component of the impedance.

25. The computer-readable medium of claim 22, wherein the logic configured to determine an inflection frequency for energy applied to the system is configured to correlate the inflection frequency for the impedance of the system to the inflection frequency for energy applied to the system using a mathematical relation.

\* \* \* \* \*